US005900246A

United States Patent [19]

Lambert

[11] Patent Number: 5,900,246

[45] Date of Patent: May 4, 1999

[54] DRUG INCORPORATING AND RELEASING POLYMERIC COATING FOR BIOPROSTHESIS

[75] Inventor: Thomas L. Lambert, Las Vegas, Nev.

[73] Assignee: Cedars-Sinai Medical Center, Los Angeles, Calif.

[21] Appl. No.: 08/464,381

[22] Filed: Jun. 5, 1995

Related U.S. Application Data

[62] Division of application No. 08/385,373, Feb. 7, 1995, Pat. No. 5,562,922, which is a continuation of application No. 08/033,394, Mar. 18, 1993, abandoned.

[51] Int. Cl.[6] ........................ A61M 25/00; A61M 25/10; A61F 2/24; G02C 7/04

[52] U.S. Cl. ......................... 424/429; 424/427; 604/264; 604/915; 623/2; 623/3; 427/2.1; 427/2.24; 427/2.28

[58] Field of Search .................................... 424/486, 423, 424/427, 429; 604/264, 266, 915; 623/2, 3; 427/2.1, 2.24, 2.28; 428/423.1

[56] References Cited

U.S. PATENT DOCUMENTS

| | | | |
|---|---|---|---|
| Re. 32,991 | 7/1989 | Szycher et al. | 528/75 |
| 3,585,647 | 6/1971 | Gajewski et al. | 3/1 |
| 3,853,804 | 12/1974 | Yen et al. | 260/32.6 N |
| 4,292,965 | 10/1981 | Nash et al. | 128/260 |
| 4,447,590 | 5/1984 | Szycher et al. | 528/76 |
| 4,582,717 | 4/1986 | von Bittera et al. | 427/2 |
| 4,614,787 | 9/1986 | Szycher et al. | 424/447 |
| 4,713,402 | 12/1987 | Solomon | 523/112 |
| 4,731,080 | 3/1988 | Galin | 623/6 |
| 4,749,585 | 6/1988 | Greco et al. | 427/2 |
| 4,869,909 | 9/1989 | Takahashi et al. | 424/486 |
| 4,879,135 | 11/1989 | Greco et al. | 427/2 |
| 4,925,668 | 5/1990 | Khan et al. | 424/422 |
| 5,019,096 | 5/1991 | Fox, Jr. et al. | 623/1 |
| 5,053,048 | 10/1991 | Pinchuk . | |
| 5,066,298 | 11/1991 | Hess | 606/194 |
| 5,118,779 | 6/1992 | Szycher | 528/75 |
| 5,183,663 | 2/1993 | Greiner | 424/443 |
| 5,451,424 | 9/1995 | Solomon et al. . | |

FOREIGN PATENT DOCUMENTS

| | | |
|---|---|---|
| 0207624 | 1/1987 | European Pat. Off. . |
| 0405284 | 1/1991 | European Pat. Off. . |
| 0520160 | 12/1992 | European Pat. Off. . |
| WO89 04682 | 6/1989 | WIPO . |
| WO92 11877 | 7/1992 | WIPO . |
| WO92 15286 | 9/1992 | WIPO . |

*Primary Examiner*—Edward J. Webman
*Attorney, Agent, or Firm*—Pretty, Schroeder & Poplawski

[57] ABSTRACT

In accordance with the present invention, there are provided prosthetic articles having polyurethane coatings with biologically active compounds incorporated within the interstices of the polymer. Methods for the preparation of such articles are also provided. Thus, a polyurethane coating is applied to a prosthetic article, the coating then swelled (without significantly dissolving the polymer) so that substantial quantities of biologically active compounds can be incorporated within the interstices of the polymer. Upon long term exposure of a prosthetic article of the invention to physiological conditions, the biologically active compound is slowly released by the treated polymer. The biologically active compound is, therefore, released only at the site where it is desired, i.e., where the prosthetic article is positioned.

21 Claims, No Drawings

DRUG INCORPORATING AND RELEASING POLYMERIC COATING FOR BIOPROSTHESIS

This is a division of application Ser. No. 08/385,373, filed Feb. 7, 1995, now U.S. Pat. No. 5,562,022 which is a continuation of application Ser. No. 08/033,394 filed Mar. 18, 1993, now abandoned.

FIELD OF THE INVENTION

The present invention relates to methods for localized drug delivery, as well as compositions and articles useful therefor.

BACKGROUND OF THE INVENTION

Currently, balloon angioplasty induced vascular injury resulting in smooth muscle proliferation contributes to a restenosis rate in excess of forty percent, leading to repeat angioplasty and bypass surgery. Despite numerous basic and clinical research efforts employing antiproliferative, antiplatelet, and antiinflammatory drugs given systemically, no effective therapy has been found in humans (McBride et al., *New Eng. J. Med.*, 318 (26):1734–1737 (1988); Liu et al., *Circulation*, 79 (6) :1374–1387 (1989)). Increasing the systemic dose of drugs to higher and potentially efficacious levels would also lead to increased toxicity in other organs. Clearly a need exists for a system that concentrates drugs locally without achieving significant systemic levels.

In one approach to prevent restenosis, researchers have attempted to deliver drugs locally in the vessel wall. However, the best means of local delivery has not been established, and very little is known of the pharmacokinetics of drugs within the vessel wall and the toxicology of large doses of drug on the integrity of the vessel. Kinetic studies of drugs delivered locally into the vessel wall to date have shown that elution of drug from the vessel wall is rapid, thus diminishing the effectiveness of the drug.

Drug delivery from polyurethanes has previously been demonstrated. For example, Kim showed that Biomer™, a hydrophobic polymer, could release prostaglandins in vitro and affect platelet aggregation despite a long period of storage (McRea and Kim, *Trans. Am. Soc. Artif. Intern. Organs*, 24:746–752 (1978); McRea et al., *Trans. Am. Soc. Artif. Intern. Organs*, 27:511–516 (1981)). He noted varying rates of release of compounds from that polymer but did not investigate these differences further. Release of heparin from intravascular catheters in quantities sufficient to decrease thrombosis on the catheter has been achieved by either covalently bonding a charged molecule to a polymer or incorporating a large nonmobile charged molecule on the surface of a polymer (Grode et al., *J. Biomed. Mater. Res. Symp.*, 3:77 (1972); Barbucci et al., *Biomaterials*, 10:299–307 (1989)). This technology has been used for antibiotics but has not been expanded to the incorporation of other drugs (Henry et al., *J. Thorac. Cardiov. Surg.*, 82:272–277 (1981)).

Recently, silicone based polymers which are capable of delivering various compounds have been implanted perivascularly, but the effect of drug was overshadowed by the inflammatory response to the polymer (Villa et al., *The Restenosis Summit IV*, 4:24 (1992)).

Polyvinyl alcohol based polymer beads, which are capable of delivering large quantities of heparin locally, have inhibited intimal hyperplasia when placed in the perivascular tissue in rats (Okada et al., *Neurosurgery*, 25:892–898 (1989)). However, clinical application for bead placement requiring surgery is limited.

Delivery of drug from a stent coating has previously been attempted. Cox incorporated methotrexate and heparin in a cellulose ester stent coating, but failed to show a reduction in restenosis when implanted in porcine coronary arteries (Cox et al., *Circulation*, 84 (4): II-71 (1991)). Local delivery of drug was not quantified, and it was not clear whether tissue levels were sufficient to block smooth muscle proliferation or whether tissue drug concentration was sufficient, but caused additional injury.

There is, therefore, a clear need in the art for means for the localized delivery of biologically active compounds to a subject, particularly to vascular tissue of a subject.

BRIEF DESCRIPTION OF THE INVENTION

In accordance with the present invention, it has been discovered that polyurethane coatings on prosthetic articles can be swelled (without significantly dissolving the polymer) so that substantial quantities of biologically active compounds can be incorporated within the interstices of the polymer. Swelling of the polyurethane allows drug uptake throughout the matrix which provides higher drug content than surface binding techniques.

Upon long term exposure of a prosthetic article to physiological conditions, the biologically active compound is slowly released by the treated polymer. The biologically active compound is, therefore, released and concentrated only at the site where it is desired, i.e., where the prosthetic article is positioned. When the target tissue is in contact with the polyurethane, the biologically active compound distributes in the tissue by passive diffusion. Increasing the lipid solubility of the compound slows release from the polyurethane, and increases the tissue retention. More lipid soluble compounds are, therefore, preferred agents for use in the practice of the present invention.

DETAILED DESCRIPTION OF THE INVENTION

In accordance with the present invention, there is provided a method for preparing a system suitable for localized delivery of biologically active compounds to a subject. The invention method comprises subjecting a medical grade polyurethane coated substrate, and a coating expansion solution (comprising at least about 0.1 part of at least one biologically active compound per 100 parts of a suitable organic solvent system) to conditions suitable to allow penetration of the biologically active compound substantially throughout the entire thickness of the polyurethane coating. Preferably, the substrate has a polyurethane coating thickness of at least about 20 microns. The solvent treated article is then dried under conditions sufficient to substantially eliminate organic solvent from the polyurethane coating.

In accordance with another embodiment of the present invention, there is provided a drug delivery system prepared as described above. Such a drug delivery system comprises a substrate having coated thereon a thickness of at least about 20 microns of a linear, aliphatic polyurethane elastomer coating, and at least one biologically active compound absorbed into the interstices of said coating.

In accordance with yet another embodiment of the present invention, there is provided a method for the localized delivery of biologically active compounds to a subject. This invention method comprises implanting the above-described delivery system at a site where the targeted release of said biologically active compound is desired.

Biologically active compounds suitable for use in the practice of the present invention may fall anywhere on the spectrum from lipophilic to hydrophilic. However, the method for preparing a system suitable for localized delivery of biologically active compounds will vary depending on the compatibility of the solubility characteristics of the polyurethane coating and the biologically active compounds to be incorporated therein. If, for example, the polyurethane coating is lipophilic and the biologically active compound is hydrophilic, it may be necessary to link the hydrophilic drug to a lipophilic carrier in order to achieve penetration of the biologically active compound through the entire thickness of the polyurethane coating. Alternatively, the polyurethane coating may be modified to make it more amenable to penetration by the biologically active compound.

Biologically active compounds suitable for use in the practice of the present invention include antithrombotic agents (e.g., hirulog, D/phenylalanyl-proloyol-L-arginyl chloromethyl ketone, and IIbIIIa receptor antagonist), anti-inflammatory drugs such as steroids, (e.g., triamcinolone acetonide, dexamethasone analogs), colchicine (Sigma, St. Louis, Mo.)), retinoids (antifibrotic) (e.g., etretinate, Retin A™), probucol (antioxidant, cholesterol lowering agent; Sigma, St. Louis, Mo.), tyrophostins, antiproliferative compounds (e.g., colchicine, sphingosine (a protein kinase C inhibitor, Sigma, St. Louis, Mo.)), angiopeptin (HBI/USA), vasodilators (e.g., molisdomine, pinacidil cGMP, CAMP, their analogs and activators), and the like. Sphingosine is of interest because of its ability to modify the polyurethane. Biologically active compounds presently preferred for use in the practice of the present invention include lipophilic compounds, for example, forskolin, sphingosine, etretinate, lipid modified oligonucleotides, and the like.

Potential modifications which might aid in improving retention of the biologically active compound by the subject include: (1) adding lipid sidechains to the biologically active compound to enhance lipid solubility and retard diffusion from lipid membranes, (2) using compounds with high affinity receptors in smooth muscle cells, (3) changing the charge of the compound to alter its diffusion kinetics, and (4) binding the biologically active compound to a substance having reactivity with a specific receptor in the target tissue. Increased uptake by the polymer, decreased elution rate from the polymer, and increased tissue retention have been demonstrated using biologically active compounds having one or more 2–18 carbon sidechains. For example, etretinate which contains a long lipid side chain showed increased uptake by the polymer, decreased elution rate from the polymer and increased tissue retention as compared to forskolin which is also lipid soluble but lacks a side chain.

Substrates suitable for use in the practice of the present invention include metallic stents, such as vascular, biliary or ureteral stents, heart valves, metallic prostheses, prosthetic joints, pacemakers, catheters, balloon coatings, ocular implants, contact lenses, and the like.

Polyurethanes employed in the practice of the present invention typically have certain flexibility, strength and biocompatibility characteristics so as to enable the application of a stable coating onto substrate (i.e., the coating will be able to withstand certain handling, deformation, abrasion, exposure to various environments, and the like, to which the resulting article will be subjected). Polyurethanes which are both biocompatible and have the above-described physical properties are characterized as being linear, aliphatic polyurethane elastomers. Suitable medical grade polyurethanes can be described as the reaction product of:

a high molecular weight polyether polyol having the structure:

$$H—(O—CH_2—CH_2—CH_2—CH_2)_n—OH$$

wherein n is such that the molecular weight of said polyether polyol falls in the range of about 500 up to 5000, with in the range of about 1 up to 5 parts, per part polyether polyol, of an aliphatic diisocyanate, and in the range of about 1 up to 5 parts, per part polyether polyol, of a chain extender.

Aliphatic diisocyanates contemplated for use in the practice of the present invention include hexamethylene diisocyanate, isophorone diisocyanate, trimethyl hexamethylene diisocyanate, dicyclohexylmethane diisocyanate, and the like. Aromatic diisocyanates may also be used in the practice of the present invention, particularly when the substrate for the polymeric coating, for example a heart valve, favors the greater rigidity associated with aromatic linkers.

Chain extenders contemplated for use in the practice of the present invention include 1,4-butanediol and other aliphatic diols.

A presently preferred polyurethane for use in the practice of the present invention is commercially available from Thermedics, Inc. (Woburn, Mass.) under the tradename Tecoflex™. A family of related polymers (and details as to the preparation thereof) is described in U.S. Pat. No. 4,447,590, incorporated by reference herein in its entirety.

Thickness of the polyurethane coating typically falls in the range of about 25 up to 500 microns. Degree of swelling of the polyurethane coating is dependent on the thickness of the coating, the solvent used for the swelling step and the time for which the solvent and coating are maintained in contact with one another. For example, a polyurethane coating having a thickness of about 50 microns can be expanded by up to about 10 times, without substantially dissolving the coating.

Coating expansion solutions contemplated for use in the practice of the present invention comprise a combination of a polymer solvent and a polymer non-solvent capable of expanding the polymer without dissolving it, wherein the ratio of solvent to non-solvent falls in the range of about 1:20 up to 1:1. Typically, the coating expansion solution contains in the range of about 1 up to 100 milligrams of at least one biologically active compound per milliliter of said organic solvent system.

The specific ratio of polymer solvent/non-solvent employed in the invention process is dependent upon a number of factors, e.g., the solubility characteristics of the specific polyurethane coating, the solubility characteristics of the biologically active compound, the relative toxicity of the components of the solvent system to the host in the event that the solvent cannot be completely evaporated from the system, and the like.

Organic solvents contemplated for use in the coating expansion solution employed in the practice of the present invention are selected from low molecular weight hydrocarbons (e.g., hexane, heptane, cyclohexane), low molecular weight alcohols (e.g., methanol, ethanol, isopropanol), polyethers (e.g., compounds of the structure:

$$R—[O—(CH_2)_x]_y—OR$$

wherein R is a lower alkyl group, x is a whole number from 1–4 and y is a whole number from 1–6, such as ethylene glycol dimethyl ether), cyclic ethers (e.g., tetrahydrofuran, tetrahydropyranoside, dioxane), chlorofluorocarbons (having in the range of about 1 up to 4 carbon atoms (e.g., dichloromethane), benzene or alkyl-substituted derivatives thereof, N,N-dimethyl acetamide, dimethylsulfoxide, as well as mixtures of any two or more thereof. A presently preferred solvent combination employed in the practice of the present invention comprises a mixture of ethanol and tetrahydrofuran in a volume ratio in the range of about 2:1 up to 20:1 (i.e., in the range of about 70 to 95% ethanol and in the range of about 5 to 30% tetrahydrofuran).

Conditions suitable to allow penetration of biologically active compound throughout the stent coating typically comprise contacting the polymer coated stent with coating expansion solution at room temperature for a time sufficient to substantially swell the coating without significantly dissolving the coating. Such time generally falls in the range of about 1 to 30 minutes and varies in accordance with the polyurethane coating and coating expansion solution chosen. For example, if the preferred polyurethane coating is contacted with a coating expansion solution containing 10% of tetrahydrofuran as the polymer solvent and ethanol as the polymer non-solvent, then a contact time of about 5–10 minutes is suitable to accomplish the desired degree of swelling of the polyurethane coating. When the tetrahydrofuran content is increased to about 25%, shorter contact times (i.e., only about 3–5 minutes) are suitable to accomplish the desired swelling of the polyurethane coating. When tetrahydrofuran content is further increased to about 40%, even shorter contact times (i.e., only about 1–3 minutes) are suitable to accomplish the desired swelling of the polyurethane coating. However, at this higher tetrahydrofuran-content, the structural integrity of the polyurethane coating is likely to be compromised if extended contact times are allowed.

The drying step contemplated for use in the practice of the present invention comprises subjecting the solvent-treated article to subjecting said substrate to a temperature in the range of about 20 up to 100° C. under reduced pressure for a time in the range of about 4 up to 16 hours. By "reduced pressure" it is meant pressure in the range of about 50–500 mm Hg, or preferably about 250 mm Hg. In a presently preferred embodiment, the solvent-treated article is initially dried by subjecting said article to room temperature at atmospheric pressure, for a time in the range of about 2 up to 15 minutes to avoid irregularities in the polymer that might occur during heat drying.

The dried article can be rinsed in saline and should be gas sterilized prior to implantation. Appropriate procedures for implantation of articles of the present invention are well known to those of skill in the art. Of course, the appropriate procedures will vary in accordance with the nature of the article selected to act as the substrate as well as their specific uses.

The invention will now be described in greater detail by reference to the following non-limiting examples.

EXAMPLE 1

Drug Incorporation into Polyurethane-Coated Articles

Nitinol stents or stainless steel coils with surface area similar to nitinol stents were coated with Tecoflex 85A™ polyurethane to a thickness of about 50 microns in accordance with the manufacture's instructions for coating metal surfaces. Stents were then incubated in solutions containing the lipophilic dyes: rhodamine B or fluorescein dilaurate (Sigma, St. Louis, Mo.), or a solution of unlabeled (Calbiochem, La Jolla, Calif.), and tritiated forskolin (New England Nuclear, Boston, Mass.) with a specific activity of 10 $\mu$Ci/mg. Forskolin, an adenylate cyclase activator with antiplatelet aggregation, antismooth muscle proliferation, and vasorelaxant properties, was selected for its lipid solubility and availability in tritiated form (Tandon et al., *Blood*, 67: (2):366–372 (1986); Vargas et al., *Transplant Proceedings*, 21 (4):3702–3704 (1989); Wood et al., *Br. J. Pharmacology*, 96:718–724 (1989)).

The drug loading procedure is carried out as follows: The desired compound is dissolved in a solution containing 3 parts ethanol and 1 part tetrahydrofuran (100 mg/ml for rhodamine B and 50 mg/ml for fluorescein dilaurate and forskolin). Subsequently, 20 mg/ml was used for in vivo stents containing forskolin and etretinate.

When a hydrophilic compound such as hirulog was loaded in the polyurethane, the polyurethane was first loaded with sphingosine or any charged lipophilic molecule as described above. With this modification, the polyurethane will swell in organic solutions containing up to 10% water. The desired compound was then dissolved as 50 mg/ml in ethanol/tertrahydrofuran/water in a ratio of 65/25/1–20. The water content will vary according to the solubility of the desired compound in this solvent system.

After incubation, all stents, coils, and films were dried overnight at 40° C. at reduced pressure. To evaluate the ability of a charged lipid soluble drug to facilitate uptake and release of a water soluble compound, thin films containing 20 mg of polyurethane with or without 1 mg of sphingosine were produced by pour plating and drying overnight at 40° C. under reduced pressure. The films were then incubated in a solution of fluorescein disodium, a water soluble dye. After incubation, films were dried as described above.

EXAMPLE 2

In Vitro Drug Release

In order to assess in vitro drug release, nitinol stents or stainless steel coils (coated with polyurethane as described in Example 1) were treated as follows. After a 15 minute preincubation (wash step), stents, coils, or films were incubated for 2–3 days in 2 ml. of phosphate buffered saline (pH=7.4) or 5% bovine serum albumin in PBS at 37° C. in a shaking water bath. At various times (as indicated in Table 1), media was removed and aliquots analyzed for dye or forskolin content. At the end of incubations, the polyurethane was dissolved in tertrahydrofuran and an aliquot analyzed to determine the quantity of compound remaining in the polymer. Serially diluted aliquots containing Rhodamine B, fluorescein dilaurate, and fluorescein disodium were measured for light absorption at 580, 491, and 491 λ, respectively, and content determined by comparison to absorption curves of control solutions. Solutions containing fluorescein dilaurate required addition of 200 $\mu$l of 10M sodium hydroxide to convert the fluorescein dilaurate into its colored form (release the two 16-carbon fatty acid dilaurate chains from the water soluble fluorescein molecule). Forskolin content was determined by scintillation counting. Results are presented in Table 1.

TABLE 1

| Compound | Vehicle | Buffer | Release Rate ($\mu$g/hr) | | | Total |
|---|---|---|---|---|---|---|
| | | | Day 1 | Day 2 | Day 3 | (mg) |
| A. Single Drug | | | | | | |
| Rhodamine B (n* = 3) | Coil | PBS | 37.0 | 5.2 | ND* | 1.5 |
| Forskolin (n = 3) | Stents | PBS | 3.8 | 3.9 | 1.6 | 4.4 |

TABLE 1-continued

| Compound | Vehicle | Buffer | Release Rate (μg/hr) Day 1 | Day 2 | Day 3 | Total (mg) |
|---|---|---|---|---|---|---|
| Fluorescein dilaurate | Coil (n = 1) | 5% BSA | 3.4 | 2.3 | ND | ND |
| Fluorescein dilaurate | Film (n = 2) | 5% BSA | 4.6 | 3.7 | ND | ND |
| B. Dual Drug | | | | | | |
| Fluorescein disodium (n = 2) | Film | | 4.0 | 1.8 | 1.8 | 0.3 |
| Fluorescein disodium (n = 2) | Film + SPH | | 16.0 | 4.0 | 2.0 | 1.1 |

*ND = not determined
*n = number of subjects

As shown in Table 1A, release rates from the polyurethane vary with water solubility. Rhodamine B, the most water soluble of the group, exhibits the highest initial release rate. Forskolin, which is less soluble in aqueous solutions, concentrates to a greater extent in the hydrophobic polymer and exhibits slower release rate. Fluorescein dilaurate is insoluble in water and required 5% albumin to promote release. Table 1B reveals improved total content of fluorescein disodium, a water soluble compound, with the addition of sphingosine (SPH) to the matrix and a subsequently higher delivery rate.

The results of this example demonstrate that polyurethane stent coatings can concentrate and release lipophilic drugs in vitro. While uptake improves with increasing lipid solubility, release rates increase with water solubility. Since albumin is the major blood carrier of lipophilic molecules, in vitro release experiments which include albumin probably better simulate in vivo conditions, especially for very hydrophobic molecules such as fluorescein dilaurate. Addition of a charged lipid-soluble molecule such as sphingosine can modify the polyurethane matrix to allow uptake of water soluble molecules.

EXAMPLE 3

Delivery of Forskolin to the Vascular Wall from a Polyurethane Coated Nitinol Stent For these experiments, nitinol stents were coated with Tecoflex™, to a thickness of about 50–100 microns, and then incubated in a solution containing unlabelled and tritiated forskolin with a specific activity of 25 μCi/mg. Resulting stents contained approximately 1.5 mg. of forskolin in approximately 20 mg of 50–100 micron thick polymer matrix coating.

Thirteen 3.5 kg. New Zealand white rabbits were anesthetized with intravenous xylazine and ketamine. The left femoral and right carotid arteries were surgically exposed, a 6 F french sheath placed in the left femoral artery, and a 22 g. angiocath placed in a branch of the common carotid. A 2.5 mm transit time flow probe (Transonics) was placed just proximal to the carotid bifurcation. After a 1000 u intraarterial bolus of heparin, a polyurethane coated nitinol stent loaded on a 3.0 mm PTCA balloon catheter was passed via the right femoral artery sheath and deployed in the right carotid artery by balloon expansion followed by catheter removal. Serial carotid blood flow measurements and blood samples proximal and distal to the deployed stent were collected to calculate forskolin blood levels.

To quantify acute tissue uptake, 6 rabbits received a drug-containing coated stent for 4 hours, and in 3 animals stents remained in situ for 24 hours before euthanasia under anesthesia was performed. To quantify tissue washout of drug, 4 stents were removed at 2 hours with the recovery catheter advanced from the femoral artery. Two animals survived for 2 hours and two for 24 hours prior to euthanasia.

For tissue processing, samples of adventitia were removed and the carotid artery was sectioned into 1 cm. proximal to the stent, vessel overlying the stent, and 1 cm. increments distal to the stent. Additional samples were obtained from strap muscle, facia, and peritracheal fat adjacent to the stent, contralateral carotid artery, liver and kidney. Tissue samples were weighed (10±6 mg for media, 12±7 for adventitia, and 23±12 for other tissues) immediately after collection and digested in 1 ml. of BTS-450 (Beckman, Fullerton, Calif.) at 40° C. for 24 hours and counted for one minute in 10 cc of Ready Organic scintillation fluid (Beckman, Fullerton, Calif.). Blood samples (0.5 ml.) were digested in 1.5 ml of 1:2 BTS-450/isopropanol at 40° C. for 24 hours, decolorized with $H_2O_2$ and counted in 18 ml. of Safety Sol™ scintillation fluid (RPI). Scintillation fluid contained 0.7% acetic acid to reduce chemiluminescence.

Instantaneous blood release rates were calculated by the following formula using the conservation of mass principle:

$$dM/dT = Q(C2 - C1)$$
$$(\text{mg/min} = \text{ml/min(mg/ml)})$$

where dM=change in mass, dT=change in time, M=mass, Q=flow, C1=upstream concentration, and C2=downstream concentration. Scintillation counts were then adjusted for measured background and efficiency. The amount of forskolin present was calculated by comparison of tissue activity to a 25 uCi/mg standard. For comparison of tissue and blood forskolin concentrations, blood levels were divided by specific gravity of rabbit blood (1.050 g/ml). Statistical analysis to assess differences between the multiple sites of the tissue samples was by one-way analysis of variances (ANOVA). If significant differences were found ($p<0.05$), pairwise comparisons were then performed using the t-test within ANOVA corrected for multiple comparisons (Bonferoni/Least Significant Difference tests).

Following stent delivery, carotid artery flow increased and remained elevated in all cases [10.3±4.2 ml/min vs. 15.9±2.6 ml/min at 1 min. ($p<0.005$) and 19.6±4.4 ml/min at 60 min. ($p<0.0001$)]. Blood levels revealed an immediate forskolin level of 57 ng/ml followed by a gradual increase to a peak level of 140 ng/ml at three to four hours. The calculated instantaneous release rate of forskolin into the bloodstream was initially 6900 ng/min which then decreased to 700 ng/min over four hours.

The local concentration of forskolin in the removed vascular and organ tissues was determined. Media overlying the stent contained 450 times the concentration of forskolin in the blood and 385 times the concentration of forskolin in the contralateral artery. Adventitia overlying the stent contained 360 times the concentration of forskolin in the blood and 305 times the concentration of forskolin in the contralateral artery. Vessel 1 cm. proximal to the stent, media and adventitia overlying the stent, and sections one and two centimeters distal to the stent all had significant levels of forskolin when compared to contralateral artery and blood $p<0.001$.

In a similar model, etretinate, a retinoic acid analog, develops concentrations in the media of 250 ng/mg tissue at 24 hours. At 24 hours, this concentration was over 2000 times the concentration in the blood. Etretinate concentrations of 185 ng/mg tissue were observed after 72 hours of implantation. In addition, ten percent of the etretinate remained in the vessel wall 4 days after removal of coated stents containing etretinate when the stent had been implanted for 72 hours.

The radial and longitudinal diffusion of forskolin at various points proximal, distal, and radial to the stent show that there is a diffusion gradient in both longitudinal and radial directions away from the stent.

Twenty four hour implants (n=3) produced media levels of 4.9±1.2 ng/mg tissue with concomitant blood level of 68±18 ng/ml giving a tissue to blood ratio of 77±22. Adventitia contained 4.1±1.8 ng FSK/mg tissue with a tissue to blood ratio of 61±18.

In drug washout experiments, all four stents were successfully removed. Media overlying the stent contained 1.2 ng FSK/mg tissue at two hours and 0.2 ng FSK/mg at 24 hours. Adventitia contained 1.7 ng/mg at 2 hours and 0.1 ng/mg at 24 hours. Other adjacent tissues all contained <0.6 ng/mg at two hours and <0.1 ng/mg at 24 hours.

These data demonstrate that a polyurethane coated nitinol stent is capable of delivering a lipophilic drug in high local concentration in the vessel wall. The large 450 fold differential of local tissue levels of forskolin over blood levels reflects the capability of this delivery system to provide high local concentration and potentially higher efficacy, with lower risk of systemic side effects. Diffusion of drug appears to follow a concentration gradient from stent to media then both radially and longitudinally into adjacent tissue. Release rates in vivo were also 10 fold greater than the in vitro release rate (7.0 ug/min vs. 0.5 ug/min) probably due to increased solubility of forskolin in blood and the constant current of blood and volume of distribution not reproduced by the shaker bath. Washout of forskolin from the vessel wall was rapid, suggesting that the measured tissue levels reflect a balance of drug uptake and release from the tissue.

EXAMPLE 4

Inhibition of Thrombosis by Forskolin Eluting for a Polyurethane Coated Nitinol Stent To evaluate the thrombogenicity of polyurethane stent coatings, a rabbit carotid crush injury, low flow thrombosis model was developed. Briefly, New Zealand white rabbits (n=14) underwent anesthesia with ketamine and xylazine followed by surgical exposure of the right carotid and left femoral arteries. A 6 french sheath was placed in the left femoral artery and a 2.0 mm transit time flow probe (Transonics) was placed in the distal carotid artery. No anticoagulant was given. Repeated crush injury with a plastic coated clamp was performed at similar force for fifteen times over a one cm. distance usually producing a small decrement in flow rate. After 5 minutes, a bare or polyurethane coated nitinol stent was advanced to straddle the area of injury and balloon expanded. After a 15 minute equilibration period during which a 3.0 mm balloon occluder was placed proximal to the stent, the occluder was inflated to reduce flow to 4 ml/min. (40% of baseline). Continuous pressure monitoring via pressure transducer placed on line in the occluder inflation system was performed to ensure maintenance of consistent occlusion.

Continuous carotid artery flow and mean blood pressure were recorded by strip chart recorder. If the flow remained <0.5 ml/min, for 5 minutes, the artery was considered occluded and experiment terminated. If the artery exhibited flow <0.5 ml/min but returned to flows above 0.5 ml/min intermittent occlusion or cyclic flow variation was determined to be present. After euthanasia, the artery was removed and cut longitudinally with a scalpel. The polyurethane coating was visually inspected for defects. Presence of white or red thrombus was also noted. The time to cyclic flow (TCF) and time to occlusion (TTO) for the above-described stents are summarized in Table 2.

TABLE 2

Time to Cyclic Flow (TCF) and Time to Occlusion (TTO) for Forskolin Treated and Control Stents

| | TCF (min) | TTO (min) |
|---|---|---|
| Uncoated (n = 5) | 16 ± 13 | 19 ± 18 |
| Polymer Coated (n = 4) | 27 ± 17 | 54 ± 27 (a) |
| Forskolin Treated (n = 5) | 208 ± 71 (b) | >240 |

(a) $p < 0.02$ compared to uncoated.
(b) $p < 0.0001$ compared to coated and uncoated.

Two of the uncoated stents, all of the coated stents, and one of the forskolin impregnated stents exhibited cyclic carotid blood flow. As seen in Table 2, impregnation of forskolin into the polyurethane remarkably increased the time to cyclic flow (TCF) and time to occlusion (TTO). In comparison, coating with polyurethane alone only had a modest impact on time to occlusion and no significant increase in time to cyclic flow. Upon visual inspection, uncoated stents appeared to have mixed red and white thrombus, coated stents had predominately white thrombus, and one forskolin impregnated stent had red thrombus only.

These results suggest that forskolin released from the polyurethane is biologically active and prevented thrombosis of the stented segment compared to uncoated and coated stents. Absence of platelet rich white thrombus in the forskolin treated stent segments suggests that inhibition of platelet aggregation decreased thrombus formation.

While the invention has been described in detail with reference to certain preferred embodiments thereof, it will be understood that modifications and variations are within the spirit and scope of that which is described and claimed.

That which is claimed is:

1. A drug delivery system for localized delivery of a biologically active compound to a subject, comprising:

a substrate having coated thereon a medical grade, linear, aliphatic polyurethane elastomer and at least one biologically active compound absorbed into the interstices of said coating, wherein said substrate is selected from the group consisting of a stent, a prostheses, a heart valve, a pacemaker, a catheter, a balloon, an ocular implant, and a contact lens, wherein said linear aliphatic polyurethane elastomer coating has a thickness of at least 20 microns, wherein said linear, aliphatic polyurethane elastomer coating is the reaction product of a) polytetramethylene ether glycol, b) an aliphatic diisocyanate, and c) a chain extender, and wherein said chain extender is an aliphatic diol.

2. The drug delivery system of claim 1 wherein the biological agent is absorbed substantially throughout the entire thickness of the polyurethane elastomer coating.

3. The drug delivery system of claim 2 wherein the polyurethane polymer coating has a thickness in the range of about 25 up to 500 microns.

4. The drug delivery system of claim 3, wherein the polytetramethylene ether glycol has a molecular weight in the range of about 500 to about 5000.

5. The drug delivery system of claim 4, wherein the ratio of chain extender to polytetramethylene ether glycol is in the range of about 1:1 to 5:1.

6. The drug delivery system of claim 5, wherein the chain extender is 1,4 butane diol.

7. The drug delivery system of claim 6, wherein said aliphatic diisocyanate is selected from the group consisting of hexamethylene diisocyanate, isophorone diisocyanate, trimethyl hexamethylene diisocyanate, and dicyclohexylmethane diisocyanate.

8. The drug delivery system of claim 7, wherein the aliphatic diisocyanate is dicyclohexylmethane diisocyanate.

9. The drug delivery system of claim 8, wherein said biologically active compound is a lipophilic compound.

10. The drug delivery system of claim 3, wherein the ratio of chain extender to polytetramethylene ether glycol is in the range of about 1:1 to 5:1.

11. The drug delivery system of claim 3, wherein the chain extender is 1,4 butane diol.

12. The drug delivery system of claim 3, wherein said aliphatic diisocyanate is selected from the group consisting of hexamethylene diisocyanate, isophorone diisocyanate, trimethyl hexamethylene diisocyanate, and dicyclohexylmethane diisocyanate.

13. The drug delivery system of claim 12, wherein the aliphatic diisocyanate is dicyclohexylmethane diisocyanate.

14. The drug delivery system of claim 3, wherein said biologically active compound is a lipophilic compound.

15. The drug delivery system of claim 3, wherein said prostheses is a prosthetic joint.

16. A drug delivery system for localized delivery of a biologically active compound to a subject, comprising:

a substrate having coated thereon a medical grade, linear, aliphatic polyurethane elastomer and at least one biologically active compound absorbed into the interstices substantially throughout the entire thickness of said coating, wherein said substrate is selected from the group consisting of a stent, a prostheses, a heart valve, a pacemaker, a catheter, a balloon, an ocular implant, and a contact lens, wherein said linear, aliphatic polyurethane elastomer coating has a thickness in the range of about 25 up to 500 microns, wherein said linear, aliphatic polyurethane elastomer coating is the reaction product of a) polytetramethylene ether glycol, b) an aliphatic diisocyanate, and c) a chain extender, and wherein said chain extender is an aliphatic diol, and wherein said drug delivery system is prepared by treating the medical-grade, polyurethane polymer coating with a coating expansion solution at a temperature, under a pressure and for a time sufficient to cause the biologically active compound to penetrate into the interstices of the polymer coating, said coating expansion solution comprising the biologically active compound and an organic solvent system, wherein the organic solvent system comprises at least one solvent for the polymer coating and at least one non-solvent for the polymer coating, wherein the solvent and the non-solvent are present in the organic solvent system at a ratio of solvent to non-solvent in the range of about 1:1 to about 1:20 by volume, and wherein the biologically active compound is present in the coating expansion solution in a concentration of at least 0.1 parts per 100 parts of the organic solvent system; and then drying the thus treated polymer coating to substantially eliminate the organic solvent system.

17. The drug delivery system of claim 16, wherein said biologically active compound is a lipophilic compound.

18. A drug delivery system for localized delivery of a biologically active compound to a subject, comprising:

a substrate having coated thereon a medical grade, linear, aliphatic polyurethane elastomer and at least one biologically active compound absorbed into the interstices substantially throughout the entire thickness of said coating, wherein said substrate is selected from the group consisting of a stent, a prostheses, a heart valve, a pacemaker, a catheter, a balloon, an ocular implant, and a contact lens, wherein said linear, aliphatic polyurethane elastomer coating has a thickness in the range of about 25 up to 500 microns, wherein said linear, aliphatic polyurethane elastomer coating is the reaction product of a) polytetramethylene ether glycol, b) an aliphatic diisocyanate, and c) a chain extender, and wherein said chain extender is an aliphatic diol, and wherein said drug delivery system is prepared by treating the medical-grade, polyurethane polymer coating with a coating expansion solution at a temperature, under a pressure and for a time sufficient to cause the biologically active compound to penetrate into the interstices of the polymer coating, said coating expansion solution comprising the biologically active compound and an organic solvent system, wherein the organic solvent system comprises at least one solvent for the polymer coating and at least one non-solvent for the polymer coating, wherein the solvent and the non-solvent are present in the organic solvent system at a ratio of solvent to non-solvent in the range of about 1:1 to about 1:20 by volume, then drying the thus treated aliphatic polyurethane elastomer coating to substantially eliminate the organic solvent system.

19. The drug delivery system of claim 18, wherein said biologically active compound is a lipophilic compound.

20. The drug delivery system of claim 18, wherein the ratio of chain extender to polytetramethylene ether glycol is in the range of about 1:1 to 5:1.

21. The drug delivery system of claim 18, wherein the chain extender is 1,4 butane diol.

* * * * *